United States Patent [19]

Prücher et al.

[11] Patent Number: 4,923,869
[45] Date of Patent: May 8, 1990

[54] BENZIMIDAZOLYLPYRIDAZINONES

[75] Inventors: Helmut Prücher, Heppenheim; Rochus Jonas, Darmstadt, both of Fed. Rep. of Germany; Jaime Piulats, Barcelona, Spain; Michael Klockow, Rossdorf, Fed. Rep. of Germany

[73] Assignee: Merck Patent Gesellschaft Mit Beschrankter Haftung, Darmstadt, Fed. Rep. of Germany

[21] Appl. No.: 830,781

[22] Filed: Feb. 19, 1986

[30] Foreign Application Priority Data

Feb. 19, 1985 [DE] Fed. Rep. of Germany ....... 3505609

[51] Int. Cl.$^5$ .................... C07D 401/14; A61K 31/50
[52] U.S. Cl. .................... 514/253; 544/238; 544/239
[58] Field of Search ........................ 544/238, 239, 253

[56] References Cited

U.S. PATENT DOCUMENTS

| | | | |
|---|---|---|---|
| 4,361,563 | 11/1982 | Austel et al. | |
| 4,595,521 | 6/1986 | Petrzilka et al. | 544/239 |
| 4,599,332 | 7/1986 | Sincor | 544/239 |
| 4,699,909 | 10/1987 | Hauee et al. | 514/256 |

FOREIGN PATENT DOCUMENTS 196005  3/1986  European Pat. Off. .

Primary Examiner—Nicholas S. Rizzo
Attorney, Agent, or Firm—Millen, White & Zelano

[57] ABSTRACT

New benzimidazolylpyridazinones of the formula I

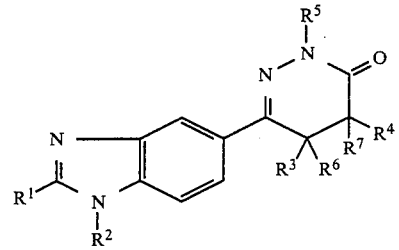

in which $R^1$ is a styryl or mononuclear of binuclear heteroaryl radial which contains 1-4 heteroatoms, each of which is unsubstituted or singly or multiply substituted by alkyl, alkoxy, alkylthio, halogen, OH, SH, amino, alkylamino, dialkylamino, acylamino having 1-8 C atoms, nitro, COOH, COOalkyl and/or CN, $R^2$, $R^3$, $R^4$ and $R^5$ are each H or alkyl, and $R^6$ and $R^7$ are each H, or together are a C—C bond, and in which the alkyl and alkoxy groups each contain 1-4 C atoms, and their salts, show positive inotropic, vasodilating and antithrombotic actions.

20 Claims, No Drawings

BENZIMIDAZOLYLPYRIDAZINONES

BACKGROUND OF THE INVENTION

The invention relates to new benzimidazolylpyridazinones.

Similar compounds are disclosed in German Offenlegungsschrift No. 2,837,161.

SUMMARY OF THE INVENTION

It is an object of this invention to provide new compounds with valuable properties, in particular those which can be used for the preparation of medicaments.

Upon further study of the specification and appended claims, further objects and advantages of this invention will become apparent to those skilled in the art.

These objects have been achieved by providing new benzimidazolylpyridazinones of Formula I

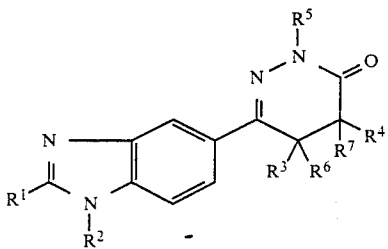

in which
$R^1$ is a styryl or mononuclear or binuclear heteroaryl radical which contains 1-4 heteroatoms, each of which is unsubstituted or singly or multiply substituted by alkyl, alkoxy, alkylthio, halogen, OH, SH, amino, alkylamino, dialkylamino, acylamino having 1-8 C atoms, nitro, COOH, COOalkyl and/or CN,
$R^2$, $R^3$, $R^4$ and $R^5$ are each H or alkyl, and $R^6$ and $R^7$ are each H, or together are a C—C bond,
and in which the alkyl and alkoxy groups each contain 1-4 C atoms,
and to their salts.

DETAILED DISCUSSION

It has been found that the compounds of the formula I and their salts have valuable pharmacological properties while being well tolerated. In particular, they exhibit an effect on the force of myocardial contraction (positive inotropic activity); furthermore, the substances have vasodilating action and thus promote blood flow. The vasodilating action and the action on the heart can be determined on, for example, anaesthetized or conscious dogs, cats, monkeys or mini-pigs, and the positive inotropic action can be determined on isolated heart preparations (for example the atrium, papillary muscle or perfused whole heart) of the rat, guinea-pig, cat or dog, for example by methods as are described in Arzneimittelforschung, Volume 31 (I) No. 1a (1981), pages 141 to 170, or by Schliep et al. in 9th International Congress of Pharmacol., London, Abstracts of papers 9P.

Furthermore, they have antithrombotic properties and properties inhibiting platelet aggregation and affecting the shape of erythrocytes. The effect on platelet function in the sense of inhibition of aggregation can be demonstrated in the rat in the Born ex vivo test (Nature 194, 927–929, 1962). The antithrombotic action is shown by the prolongation of the bleeding time by the method of Stella (Thrombos. Res. 7, 709–716, 1975), in the reduction in the thrombus weight on cold-induced thrombosis of the jugular vein in the rat by the method of Meng (Ther. Ber. 47, 69–79, 1975), and in the increase in the laser pulses necessary for complete thrombosis in the mesenteric venule of the rat, corresponding to a modification of the method of Kovacs (Microvasc. Res. 6, 194–201, 1973).

The favorable action on erythrocyte deformability is detectable by the method of Schmid-Schöbein with nucleopore filters (Pflüger's Archiv 338, 93–114, 1973). In addition, favorable effects on fibrinolysis/euglobulinlysis time can be detected by the method of v. Kaulla (Progr. Chem. Fibrinol, Thrombol. 1, 131–149, 1975; ed. J. F. Davidson, Raven Press, N.Y.).

The compounds can thus be used as active compounds in medicaments in human and veterinary medicine. Furthermore, they can be used as intermediates for the preparation of other active compounds for medicaments.

In the formulae, alkyl is preferably unbranched, preferably has 1–3 C atoms, and is preferably methyl, and is also preferably ethyl or propyl, furthermore isopropyl, butyl, isobutyl, sec.-butyl or tert.-butyl.

Alkoxy is preferably unbranched, preferably has 1–3 C atoms and is preferably methoxy, and is also preferably ethoxy or propoxy, furthermore isopropoxy, butoxy, isobutoxy, sec.-butoxy or tert.-butoxy. Alkylthio is preferably unbranched, preferably has 1–3 C atoms and is preferably methylthio, and is also preferably ethylthio or propylthio, furthermore isopropylthio, butylthio, isobutylthio, sec.-butylthio or tert.-butylthio.

Halogen is preferably F or Cl, but is also Br or I. Alkylamino is preferably methylamino, and is also preferably ethylamino or propylamino, furthermore isopropylamino, butylamino, isobutylamino, sec.-butylamino or tert.-butylamino. Dialkylamino is preferably dimethylamino, and is also preferably methylethylamino, diethylamino or dipropylamino, furthermore, for example, diisopropylamino, dibutylamino, diisobutylamino, di-sec.-butylamino or di-tert.-butylamino. Acylamino is preferably alkanoylamino having 1–8 C atoms, for example formamido, acetamido, propionamido, butyramido, isobutyramido, valeramido, hexanamido, heptanamido and octanamido, and is also preferably benzamido, substituted benzamido, for example o-, m-, or p-methylbenzamido, o-, m- or p-methoxybenzamido, 3,4-dimethoxybenzamido, o-, m- or p-methylthiobenzamido, o-, m- or p-fluorobenzamido, o-, m- or p-chlorobenzamido, o-, m- or p-bromobenzamido, o-,m- or p-iodobenzamido, o-, m- or p-aminobenzamido, o-, m- or p-methylaminobenzamido, o-, m- or p-dimethylaminobenz-amido, o-, m- or p-nitrobenzamido, o-, m- or p-carboxy-benzamido, o-, m- or p-cyanobenzamido, and is also preferably unsubstituted or substituted picolinamido, nicotinamido or isonicotinamido. COOalkyl is preferably methoxycarbonyl or ethoxycarbonyl, furthermore propoxycarbonyl, isopropoxycarbonyl, butoxycarbonyl, isobutoxycarbonyl, sec.-butoxycarbonyl, or tert.-butoxycarbonyl.

When $R^1$ stands for a substituted styryl or heteroaryl radical, the total number or heteroaryl radical is 1 to 5, preferably 1 or 2.

The possible substituents on the mentioned benzamido group include all of those mentioned for $R^1$ per se except for acylamino. The total number of substituents on the benzamido group is typically 0 to 5, preferably 0 to 1.

The mononuclear or binuclear heteroaryl radicals typically are of 3 to 14, preferably 5 to 10 ring atoms in total, each ring containing from 3 to 8, preferably 5 or 6 ring atoms in total, there being from 1 to 4, preferably 1 or 2 hetero atoms in each ring. Suitable hetero atoms include O, N and S.

Specifically, $R^1$ is preferably styryl which is unsubstituted or substituted as indicated, or 1-, 2- or 3- pyrryl, 2-or 3-furyl, 2- or 3-thienyl, 2-, 3- or 4-pyridyl, 2-, 4- or 5-thiazolyl, 3-, 4- or 5-isothiazolyl, 1-, 3-, 4- or 5- pyrazolyl, 1-, 2- or 4(5)-imidazolyl, 2- 4- or 5-oxazolyl, 3-, 4- or 5-isoxazolyl, 1,2,4-triazol-1-, -3- or -5-yl, 1,3,4-thiadiazol-2-yl, 1- or 5-tetrazolyl, 3- or 4-pyridazinyl 2-, 4- or 5-pyrimidyl, pyrazinyl, 2-, 3-, 4-, 5-, 6- or 7-indolyl, 2-, 3-, 4-, 5-, 6- or 7-benzofuryl, 2-, 3-, 4-, 5-, 6- or 7-benzothienyl, 2-, 3-, 4-, 5-, 6-, 7- or 8- quinolyl, 1-, 3-, 4-, 5-, 6-, 7- or 8-iso-quinolyl, 2-, 4-, 5-, 6- or 7-benzothiazolyl, 1-, 2-, 4-, 5-, 6- or 7- benzimidazolyl or 2-, 6- or 8-purinyl which is unsubstituted or substituted as indicated.

Individual preferred substituted radicals $R^1$ are o-, m- or p-methylstyryl, o-, m- or p-methoxystyryl, o-, m- or p-ethoxystyryl, 2,3-, 2,4- 2,5, - 2,6, -3,4- or 3,5-dimethoxystyryl, 3,4,5-trimethoxystyryl, o-, m- or p-methylthiostyryl, o-, m- or p-ethylthiostyryl, o-, m- or p-fluorstyryl, o-, m- or p-chlorostyryl, o-, m- or p-bromostyryl, o-, m- or p-iodostyryl, o-, m- or p-hydroxystyryl, o-, m- or p-mercaptostyryl, o-, m- or p-aminostyryl, o-, m- or p-methylaminostyryl, o-, m- or p-ethylaminostyryl, o-, m-or p-dimethylaminostyryl, o-, m- or p-diethylaminostyryl, o-, m- or p-formamidostyryl, o-, m- or p-acetamidostyryl, o-, m- or p-benzamidostyryl, o-, m- or p-nitrostyryl, o-, m- or p-carboxystyryl, o-, m- or p-methoxycarbonylstyryl, o-, m- or p-ethoxycarbonylstyryl, o-, m- or p-cyanostyryl, 1-methyl-2-pyrryl, 1-methyl-3-pyrryl, 3-, 4- or 5-methyl-2-furyl, 3-, 4- or 5-fluoro-2-furyl, 3-, 4- or 5-chloro-2-furyl, 5-bromo-2-furyl, 5-nitro-2-furyl, 3-, 4- or 5-methyl-2-thienyl, 3-, 4- or 5-fluoro-2-thienyl, 3-, 4- or 5- nitro-2-thienyl, 3-, 4- or 5-dimethylamino-2-thienyl, 3-, 4- or 5-formamido-2-thienyl, 2-, 4- or 5-methyl-3-thienyl, 3-, 4-, 5- or 6-methyl-2-pyridyl, 3-, 4-, 5- or 6-fluoro-2-pyridyl, 3-, 4-, 5- or 6-chloro-2-pyridyl, 2-, 4-, 5- or 6-methyl-3-pyridyl, 2-, 4-, 5- or 6-fluoro-3-pyridyl, pyridyl, 2-, 4-, 5- or 6-chloro-3-pyridyl, 2-, 4-, 5- or 6-hydroxy-3-pyridyl, 2-, 4-, 5- or 6-dimethylamino-3-pyridyl, 2-, 4-, 5- or 6-formamido-3-pyridyl, 2-, 4-, 5- or 6-acetamido-3-pyridyl, 2- or 3-methyl-4-pyridyl, 2- or 3-fluoro-4-pyridyl, 2- or 3-chloro-4-pyridyl, 2,6-dichloro-4-pyridyl, 4- or 5-methyl-2-thiazolyl, 5-nitro-2-thiazolyl, 2- or 5-methyl-4-thiazolyl, 2,4-dimethyl-5-thiazolyl, 4- or 5-methyl-3-isothiazolyl, 3- or 5-methyl-4-isothiazolyl, 4- or 5-methyl-3-pyrazolyl, 4- or 5-methyl-2-imidazolyl, 2- or 5-methyl-4-imidazolyl, 4- or 5-methyl-2-oxazolyl, 2- or 5-methyl-4-oxazolyl, 2- or 4-methyl-5-oxazolyl, 4- or 5-methyl-3-isoxazolyl, 3- or 5-methyl-4-isoxazolyl, 3- or 4-methyl-5-isoxazolyl and 5-methyl-1,3,4-thiadiazol-2-yl.

Particularly preferred radicals $R^1$ are 2-, 3- or 4-pyridyl, also 2- or 3-thienyl, 2- or 3-furyl, 1-methyl-2-pyrryl, styryl, p-dimethylaminostyryl or 3,4-dimethoxystyryl.

$R^2$, $R^4$ and $R^5$ are each preferably H or $CH_3$; in particular $R^2$, $R^4$ and $R^5$ are preferably H. $R^3$ is preferably H, $CH_3$ or $C_2H_5$, in particular $CH_3$.

$R^6$ and $R^7$ are each preferably H.

The invention particularly relates to those compounds of the formula I in which at least one of the specified radicals has one of the meanings which is indicated above as preferred. Some preferred groups of compounds can be expressed by the following part formulae Ia to Ig which correspond to the formula I and in which the unspecified radicals have the meaning indicated for formula I, but in which in Ia
  $R^1$ is 2-, 3- or 4-pyridyl, 2- or 3-thienyl, 2- or 3-furyl, 1-methyl-2-pyrryl, styryl, p-dimethylaminostyryl or 3,4-dimethoxystyryl;

in Ib
  $R^1$ is 2-, 3- or 4-pyridyl, 2- or 3-thienyl, 2- or 3-furyl, 1-methyl-2-pyrryl, styryl, p-dimethylaminostyryl or 3,4-dimethoxystyryl,
  $R^2$ $R^4$ and $R^5$ are each H or $CH_3$, and
  $R^3$ is H, $CH_3$ or $C_2H_5$;

in Ic
  $R^1$ is 2-, 3- or 4-pyridyl or 2- or 3-thienyl,
  $R^2$, $R^4$ and $R^5$ are each H or $CH_3$, and
  $R^3$ is H, $CH_3$ or $C_2H_5$;

in Id
  $R^1$ is 2-, 3- or 4-pyridyl or 2- or 3-thienyl,
  $R^2$, $R^4$ and $R^5$ are each H or $CH_3$,
  $R^3$ is H, $CH_3$ or $C_2H$, and
  $R^6$ and $R^7$ are each H;

in Ie
  $R^1$ is 2-, 3- or 4-pyridyl or 2- or 3-thienyl,
  $R^2$, $R^4$ and $R^5$ are each H or $CH_3$, and
  $R^3$ is H, $CH_3$ or $C_2H_5$, and
  $R^6$ and $R^7$ together are a C—C bond;

in If
  $R^1$ is 2-, 3- or 4-pyridyl, 2- or 3-thienyl, 2- or 3-furyl, 1-methyl-2-pyrryl, styryl, p-dimethylaminostyryl or 3,4-diemthoxystyryl,
  $R^2$ is H or $CH_3$,
  $R^3$ is $CH_3$ or $C_2H_5$, and
  $R^4$, $R^5$, $R^6$ and $R^7$ are each H;

in Ig
  $R^1$ is 2-, 3- or 4-pyridyl or 2- or 3-thienyl,
  $R^2$ is H or $CH_3$,
  $R^3$ is $CH_3$ or $C_2H_5$, and
  $R^4$, $R^5$, $R^6$ and $R^7$ are each H.

Moreover, the compounds of the formula I are prepared by methods known per se and as are described in the literature (for example in the standard works such as Houben-Weyl, Methoden der Organischen Chemie [Methods of Organic Chemistry], published by Georg Thieme, Stuttgart; but, in particular, in German Offenlegungsschrift No. 2,837,161), namely under reaction conditions which are known and suitable for the reactions mentioned. It is also possible to make use for this purpose of variants which are known per se and which are not mentioned here in detail.

Thus, the compounds of formula I and their salts can be prepared by methods wherein a diamine of the formula II

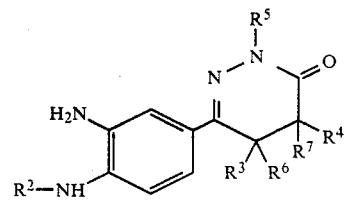

in which
$R^2$, $R^3$, $R^4$, $R^5$, $R^6$ and $R^7$ have the indicated meanings, is reacted with an acid of the formula $R^1$—COOH (in which $R^1$ has the idicated meaning) or with one of its reactive derivatives or with an aldehyde of the formula $R^1$—CHO (in which $R^1$ has the indicated meaning) in the presence of an oxidizing agent, or a compound of the formula III, which is optionally prepared in the reaction mixture,

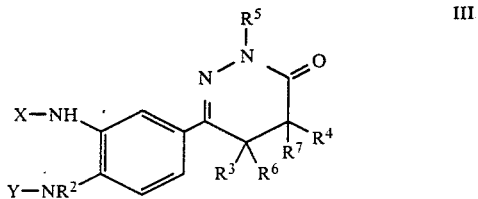

in which
one of the radicals X and Y is H,
and the other of these radicals is the group $R^1$—$CZ^1$-$Z^2$—,
$Z^1$ and $Z^2$, which can be identical or identical or different, are each
  OH or SH groups which are optionally substituted by alkyl, or together are O, S, NH, N-alkyl, alkylenedioxy or alkylenedithio, each having 2 or 3 C atoms, and
$R^1$ or $R^7$ have the indicated meanings,
is cyclized
or a keto acid of the formula IV

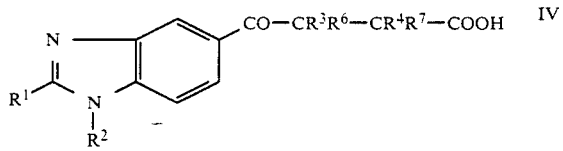

in which $R^1$, $R^2$, $R^3$, $R^4$ and $R^6$ and $R^7$ have the indicated meanings, or one of its reactive derivatives, is reacted with a hydrazine of the formula $R^5$—NH—$NH_2$ (in which $R^5$ has the indicated meaning) or with one of its reactive derivatives, and/or in that a tetrahydropyridazinone of the formula I ($R^6=R^7=H$) is converted, by treatment with dehydrogenating agents, into the corresponding dihydropyridazinone of the formula I ($R^6$ and $R^7$ together=C—C bond), and/or in that one functional group in a compound of the formula I is converted into another functional group, and in that, where appropriate, a base of the formula I is converted, by treatment with an acid, into one of its salts.

The starting materials can, if desired, also be formed in situ, in such a manner that they are not isolated from the reaction mixture but are immediately reacted further to give compounds of the formula I. On the other hand, it is possible to carry out the reaction stepwise, it being possible to isolate further intermediates.

Thus, the compounds of the formula I can be obtained by reaction of diamines of the formula II with acids of the formula $R^1$—COOH or their reactive derivatives. Particularly suitable reactive derivatives of the acids are the corresponding nitriles, acid halides, esters, amides, imidic esters, imidic thioesters, imidic acid halides, amidines, thiocarboxylic esters, dithiocarboxylic esters or ortho esters.

Some of the starting materials of the formulae II and $R^1$—COOH are known. Those which are unknown can be prepared by methods known per se, for example from German Offenlegungsschrift No. 2,837,161. The carboxylic acids of the formula $R^1$—COOH can be obtained by, for example, oxidation of corresponding aldehydes of the formula $R^1$—CHO.

In detail, the reaction of the diamines of the formula II with the acids of the formula $R^1$—COOH, or with their reactive derivatives, takes place in the presence or absence of an inert solvent, at temperatures between about −20° and about 250°, preferably between 60° and 150°. Examples of suitable solvents are hydrocarbons such as benzene, toluene, xylenes or mesitylene; halogenated hydrocarbons such as dichloromethane, trichloroethylene or chlorobenzene; tertiary bases such as triethylamine, pyridine or picolines; alcohols such as methanol, ethanol or isopropanol; glycols and glycol ethers such as ethylene glycol, diethylene glycol, or 2-methoxyethanol; ketones such as acetone; ethers such as tetrahydrofuran (THF) or dioxane; amides such as dimethylformamide (DMF), or sulfoxides such as dimethyl sulfoxide. Mixtures of these solvents are also suitable. In some cases, it is advisable to add catalytic amounts of an acid such as p-toluenesulfonic acid, or to add a dehydrating agent such as carbonyldiimidazole, phosphorus oxychloride, polyphosphoric acid or thionyl chloride, it also being possible for the dehydrating agent to act as the solvent.

If the free carboxylic acids of the formula $R^1$—COOH are used, the reaction is preferably carried out in the presence of one of the dehydrating agents mentioned and, where appropriate, of a tertiary base such as pyridine or triethylamine, preferably at temperatures between −20° and 150°. A particularly favorable method comprises the reaction of the diamine with the acid in THF in the presence of carbonyldiimidazole at room temperature.

The reaction can also be carried out stepwise. Thus, for example, it is possible partially to acylate II with an acid chloride of the formula $R^1$—COCl to give a 6-(3-$R^1$CO—NH-4-$R^2$NH-phenyl)pyridazin-3-one or a 6-(3-amino-4-$R^1$CO—$NR^2$-phenyl)pyridazin-3-one (or the corresponding 4,5-dihydropyridazin-3-ones; or to give mixtures of the isomers), which is subsequently dehydrated, for example by boiling with acetic acid, to give I.

It is also possible to use, in place of the acid, a corresponding aldehyde of the formula $R^1$—CHO when an oxidizing agent is simultaneously present. The oxidizing agent which is preferably used is sulfur in a hydrocarbon such as benzene, toluene, xylene or mesitylene, or sodium disulfite in solvents such as dimethylacetamide, in each case at temperatures between about 80° and about 200°. The aldehydes are, as a rule, known and can be obtained by, for example, formylation of the corresponding base compounds $R^1$—H, for example by the method of Vilsmeier-Haack.

The compounds of the formula I can also be obtained by cyclization of compounds of the formula III. In the latter, the radicals $Z^1$ and $Z^2$ together are preferably O.

The cyclization is preferably carried out in a solvent such as ethanol, isopropanol, acetic acid, chlorobenzene, ethylene glycol, DMF, tetralin or in an excess of the acylating agent used for the preparation of the compound of the general formula II, for example in $R^1CN$, $(R^1CO)_2O$, $R^1COOH$, $R^1CSOH$ or $R^1CSSH$ or their esters, amides or halides, at elevated temperatures, for examples at temperatures between 0° and 250°, where appropriate in the presence of a condensing agent such as phosphorus oxychloride, thionyl chloride, sulfuryl chloride, sulfuric acid, hydrochloric acid, phosphoric acid, acetic acid, acetic anhydride or, where appropriate, also in the presence of a base such as potassium ethylate or potassium tert.-butylate. However, the cylization can also be carried out without solvent and/or without condensing agent.

However, the reaction is particularly advantageously carried out in such a manner that an appropriate 6-(acylaminonitrophenl)pyridazin-3-one is converted into a corresponding compound of the formula III be reduction, for example by reduction with hydrogen in the presence of a hydrogenation catalyst such as Raney nickel, platinum or palladium/charcoal, by reduction with metals such as iron, tin or zinc, or by reduction with metal salts such as iron (II) sulfate, tin (II) chloride or chromium (II) chloride, the compound of the formula III being cyclized, where appropriate in the same reaction mixture and, if necessary, in the presence of an acid such as hydrochloric acid, sulfuric acid, phosphoric acid, acetic acid or a carboxylic acid of the formula $R^1COOH$, or in the presence of a condensing agent such as phosphorus oxychloride or in the presence of a base such as potassium ethylate, where appropriate in a solvent such as ethanol, isopropanol, ethylene glycol, DMF, dimethyl sulfoxide or chlorobenzene, at temperatures between 0° and 250°.

The compounds of the formula I can also be obtained by reaction of a keto acid of the formula IV, or of one of its reactive derivatives, with a hydrazine of the formula $R^5$—NH—$NH_2$, or one of its reactive derivatives.

The carboxylic acids of the formula IV can be prepared by methods known per se, for example in analogy to German Offenlegungsschrift No. 2,837,161.

Particularly suitable reactive derivatives of the carboxylic acids of the formula IV are the esters, for example the alkyl esters in which the alkyl group preferably has 1-4 C atoms, in particular the methyl and ethyl esters, also the nitriles, the acid halogenides, for example, acid chlorides or acid bromides, and the amides. Other suitable reactive derivatives of the carboxylic acids of the formula IV can be formed in situ during the reaction, without being isolated. These include, for example, the hydrazones of the formula Ben-C(=$NNHR^5$)—$CR^3R^6$—$CR^4R^7$—COOH and the hydrazides of the formula Ben-CO—$CR^3R^6$—$CR^4R^7$—CO—$NHNHR^5$ (in which Ben is the 1-$R^2$-2-$R^1$-5-benzimidazolyl radical).

Examples of suitable reactive derivatives of the hydrazine of the formula $R^5$—NH—$NH_2$ are the corresponding hydrazine hydrates, acetyl hydrazines, semicarbazides or carbazic esters.

For the reaction with the carboxylic acids of the formula IV, or with their reactive derivatives, it is advantageous to use 1-5 equivalents of the hydrazine, or of reactive hydrazine derivative, which can act as the solvent. However, it is preferable to add an additional inert solvent. Suitable inert solvents which are preferred are alcohols such as methanol, ethanol, isopropanool, n-butanol, isoamyl alcohol, glycols and their ethers, such as ethylene glycol, diethylene glycol, ethylene glycol monomethyl or monoethyl ether (methylglycol or ethylglycol), carboxylic acids such as formic, acetic or propionic acid, also ethers, in particular water-soluble ethers such as tetrahydrofuran, dioxane or ethylene glycol dimethyl ether (diglyme); also water and mixtures of these solvents with one another, in particular mixtures with water, for example aqueous ethanol. It is also possible to add an acid, such as sulfuric acid or p-toluenesulfonic acid, as a catalyst. The reaction temperatures are preferably between about 0° and 200°, preferably between 20° and 100°, and the reaction times are between about 1 and 48 hours.

A tetrahydropyridazinone of the formula I ($R^6=R^7=H$) can, if desired, be dehydrogenated to give a corresponding dihydropyridazinone (I, $R^6$ and $R^7$ together are a C—C bond). Examples of suitable dehydrogenating agents are bromine, $PCl_5$, sodium 3-nitrobenzenesulfonate, $CrO_3$, N-bromosuccinimide, $H_2O_2$, 2,3-dichloro-5,6-dicyano-1,4-benzoquinone (DDQ) or $NaNO_2$, in a solvent such as dioxane, acetic acid, propionic acid or nitrobenzene, at temperatures between about 0° and 120°, preferably between 50° and 100°.

It is also possible to convert, in a manner known per se, one functional group in a compound of the formula I into another functional group.

Thus, for example, OH, SH or NH groups can be alkylated to give alkoxy, alkylthio, monoalkylamino or dialkylamino groups, NH groups can be acylated to give acylamino groups, $NO_2$ groups can be reduced to give $NH_2$ groups, carboxyl groups can be esterified to give COOalkyl groups, or can be converted via the corresponding amides into CN groups, ester groups can be hydolyzed to give COOH groups, and halogen atoms can be converted with metal cyanides into CN groups. All these conversions are carried out by methods which are described in the literature (for example Houben-Weyl, loc. cit.) and are familiar those skilled in the art.

A base of the formula I can be converted with an acid into the relevant acid addition salt. Particularly suitable acids for this reaction are those which provide physiologically acceptable salts. Thus, it is possible to use inorganic acids, for example sulfuric acid, nitric acid hydrogen halide acids, such as hydrochloric acid or hydrobromic acid, phosphoric acid, such as orthophosphoric acid, and sulfamic acid, as well as organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids, and lauryl sulfuric acid. Salts with physiologically unacceptable acids, for example picrates, can be used to purify the compounds of the formula I.

An acid of the formula I can be converted by reaction with a base into one of its metal or ammonium salts; particularly suitable for this are the Na, K, Mg, Ca and ammonium salts, also substituted ammonium salts, for example the dimethylammonium, diethylammonium, monoethanolammonium, diethanolammonium, triethanolammonium, cyclohexylammonium and dicyclohexylammonium salts, furthermore dibenzylethylenediammonium salts, or salts with N-methyl-D-glucamine or with basic amino acids, such as arginine or lysine.

If desired, the free bases of the formula I can be liberated from their salts by treatment with strong bases, such as sodium or potassium hydroxide, sodium or potassium carbonate.

Compounds of the formula I may contain one or more centers of asymmetry. In this case, they are usually in the racemic form. Racemates which have been obtained can be mechanically or chemically separated into their optical antipodes by methods known per se. Preferably, diastereomers are formed from the racemic mixture by reaction with an optically active resolving agent. Examples of suitable resolving agents are optically active acids, such as the D- and L-forms of tartaric acid, diacetyltartatic acid, dibenzoyltartaric acid, mandelic acid, maleic acid, lactic acid or the various optically active camphorsulfonic acids, such as β-camphorsulfonic acid.

Of course, it is also possible to obtain optically active compounds of the formula I by the methods described above in which the starting materials used are already optically active.

The invention also relates to the use of the compounds of the formula I and of their physiologically acceptable salts for the preparation of pharmaceutical formulations, in particular by non-chemical means. For this purpose, they can be converted into a suitable administration form together with at least one solid, liquid and/or semiliquid vehicle or auxiliary and, where appropriate, in combination with one or more other active compounds.

The invention also relates to agents, in particular pharmaceutical formulations, containing at least one compound of the formula I and/or one of its physiologically acceptably salts.

These formulations can be used as medicaments in human or veterinary medicine. Suitable vehicles are organic or inorganic substances which are suitable for eternal (for example oral), parenteral or topical administration and which do not react with the new compounds, for example water, vegetable oils, benzyl alcohols, polyethylene glycols, glycerol triacetate, gelatin, carbohydrates such as lactose or starch, magnesium stearate, talc and vaseline. In particular, tablets, coated tablets, capsules, syrups, elixirs or drops are used for oral administration, suppositories for rectal administration, solutions, preferably oily or aqueous solutions, also suspensions, emulsions or implants, for parenteral administration, and ointments, creams or powders for topical administration. It is also possible to freeze-dry the new compounds and to use the resulting lyophilizates for the preparation of, for example, products for injection. The formulations indicated can be sterilized and/or contain auxiliaries such as lubricants, preservatives, stabilizers and/or wetting agents, emulsifiers, salts to affect the osmotic pressure, buffer substances, colorants, flavorings and/or perfumes. They can, if desired, also contain one or more other active compounds, for example one or more vitamins.

The invention also relates to the use of the compounds of the formula I for controlling diseases, in particular cardiace insufficiency, and to their use for the therapeutic treatment of the human or animal body.

This entails the substances according to the invention being, as a rule, administered in analogy to known substances having a positive inotropic effect, such as amrinone, preferably in doses between about 1 and 100 mg, in particular between 2 and 20 mg, per dosage unit. The daily dose is preferably between about 0.02 and 2 mg/kg of body weight. However, the specific dose for each particular patient depends on a very wide variety of factors, for example on the activity of the specific compound used, on the age, body weight, generaly state of health, sex, on the diet, on the time and route of administration, on the rate of excretion, the medicament combination and the severity of the particular disease to which the thereapy is applied. Oral administration is preferred. Compared with the digitalis glycosides hitherto used for the therapy of cardiac insufficiency, the compounds of the formula I are distinguished by an improved therapeutic range and peripheral relief.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

In the examples which follow, "usual working up" means: if necessary, water or dilute sodium hydroxide solution if added, extraction is carried out with an organic solvent such as ethyl acetate, chloroform or dichloromethane, the organic phase is separated off, dried over sodium sulphate, filtered and evaporated, and purification by chromatography and/or crystallization is carried out.

EXAMPLE 1

A mixture of 17 g of isonicotinoyl chloride, 21.8 g of 5-methyl-6-(3,4-diaminophenyl)-4,5-dihydropyridazin-3-one ("IIa"; m.p. 195°–196°) and 400 ml of chlorobenzene is boiled for 2 hours. After having been cooled, the usual working up is carried out and, initially, an oily mixture of 5-methyl-6-(3-amino-4-isonicotinamidophenyl)- and 5-methyl-6-(3-isonicotinamido-4-aminophenyl)-4,5-dihydropyridazin-3-one is obtained, which is dissolved in 400 ml of acetic acid and boiled for 3 hours. After having been cooled, 5-methyl-6-[2-(4-pyridyl)-5-benzimidazolyl]-4,5-dihydropyridazin-3-one ("M"), dihydrate, m.p.195°–198° (decomposition) is obtained. Dihydrochloride-dihydrate, m.p. 224°–227°. Methanesulphonate, m.p. 282°–285°.

The following 5-methyl-6-(2-$R^1$-5-benzimidazolyl-4,5-dihydropyridazin-3-ones are obtained analogously using the appropriate acid chlorides:

$R^1$ = styryl, hydrochloride. decomposition above 306°
  p-methylstyryl
  o-methoxystyryl
  m-methoxystyryl
  p-methoxystyryl, hydrochloride-monohydrate, decomposition above 306°
  3,4-dimethoxystyryl, hydrochloride, decomposition above 285°
  3,4,5-trimethoxystyryl
  p-methylthiostyryl
  o-fluorostyryl
  m-fluorostyryl
  p-fluorostyryl
  o-chlorostyryl
$R^1$ = m-chlorostyryl
  p-chlorostyryl
  p-bromostyryl
  p-iodostyryl
  p-hydroxystyryl
  p-mercaptostyryl
  p-aminostyryl
  p-methylaminostyryl
  o-dimethylaminostyryl
  m-dimethylaminostyryl
  p-dimethylaminostyryl, hemihydrate. decomposition above 268°

-continued

| | |
|---|---|
| | p-acetamidostyryl |
| | p-nitrostyryl |
| | p-carboxystyryl |
| | p-methoxycarbonylstyryl |
| | p-ethoxycarbonylstyryl |
| | p-cyanostyryl |
| | 2-pyrryl |
| | 1-methyl-2-pyrryl, hydrochloride, decomposition above 324° |
| | 2-furyl, hydrochloride, decomposition above 276° |
| | 5-methyl-2-furyl |
| | 5-bromo-2-furyl |
| | 5-nitro-2-furyl |
| | 3-furyl |
| | 2-thienyl, hydrochloride, decomposition above 316° |
| | 5-methyl-2-thienyl |
| | 5-methoxy-2-thienyl, |
| | 5-chloro-2-thienyl, m.p. 310–313° |
| | 4-bromo-2-thienyl, hydrochloride-monohydrate, m.p. 304–306° |
| | 5-bromo-2-thienyl, hydrochloride, m.p. 313–315° |
| | 5-nitro-2-thienyl |
| | 5-cyano-2-thienyl, hydrochloride-hemihydrate, decomposition above 303° |
| | 3-thienyl, hydrochloride, m.p > 300° |
| | 2-pyridyl, hydrochloride-monohydrate, decomposition above 222° |
| | 6-methyl-2-pyridyl, dihydrochloride-hemihydrate, decomposition above 312° |
| | 3-pyridyl, dihydrate, decomposition above 173° |
| $R^1 =$ | 4-chloro-3-pyridyl |
| | 2,6-dichloro-4-pyridyl |
| | 4-thiazolyl |
| | 4-methyl-2-thiazolyl |
| | 2,4-dimethyl-5-thiazolyl |
| | 3-pyrazolyl, hydrochloride-hemihydrate, no m.p. up to 320° |
| | 5-methyl-3-pyrazolyl |
| | 2-imidazolyl |
| | 4(5)-imidazolyl |
| | 2-methyl-4(5)-imidazolyl |
| | 5-methyl-4-imidazolyl, dihydrochloride-monohydrate, no m.p. up to 320° |
| | 3-isoxazolyl |
| | 1,2,4-triazol-5-yl |
| | pyrazinyl |
| | 4-indolyl, hydrochloride-hydrate, decomposition above 338° |
| | 5-indolyl |
| | 2-quinolyl |
| | 4-quinolyl |
| | 1-isoquinolyl. |

EXAMPLE 2

A mixture of 12.3 g of isonicotinic acid, 23.2 g of 5-methyl-6-(3-amino-4-methylaminophenyl)-4,5-dihydropyridazin-3-one, 16.2 g of N,N'-carbonyldiimidazole and 600 ml of THF is stirred at 25° for 16 hours. After the usual working up, an oily mixture of 5-methyl-6-(3-amino-4-N-methylisonicotinamidophenyl)- and 5-methyl-6-(3-isonicotinamido-4-methylaminophenyl)-4,5-dihydropyridazin-3-one is obtained and is dissolved in 400 ml of acetic acid. After the solution has been boiled for 3 hours, then cooled and submitted to the usual working up, 5-methyl-6-[1-methyl-2-(4-pyridyl)-5-benzimidazolyl]-4,5-dihydropyridazin-3-one is obtained; dihydrochloride, decomposition above 298°.

The following 5-methyl-6-(1-methyl-2-$R^1$-5-benzimidazolyl)-4,5-dihydropyridazin-3-ones are obtained analogously using the corresponding acids:

| | |
|---|---|
| $R^1 =$ | styryl |
| | p-methylstyryl |
| | p-methoxystyryl |
| | 3,4-dimethoxystyryl |
| | p-fluorostyryl |
| | p-chlorostyryl |
| | p-dimethylaminostyryl |
| | 2-pyrryl |
| | 1-methyl-2-pyrryl |
| | 2-furyl |
| | 5-methyl-2-furyl |
| | 3-furyl |
| | 2-thienyl |
| | 3-thienyl |
| | 2-pyridyl, hydrochloride-dihydrate, decomposition above 245° |
| | 6-methyl-2-pyridyl |
| | 3-pyridyl, dihydrochloride-hydrate, decomposition above 222° |
| | 4-chloro-3-pyridyl |
| | 2,6-dichloro-4-pyridyl |
| | 4-thiazolyl |
| | 4-methyl-2-thiazolyl |
| | 2,4-dimethyl-5-thiazolyl |
| | 3-pyrazolyl |
| | 5-methyl-3-pyrazolyl |
| | 2-imidazolyl |
| | 4(5)-imidazolyl |
| | 2-methyl-4(5)-imidazolyl |
| | 1,2,4-triazol-5-yl |
| | 4-quinolyl. |

Analogously from 5-methyl-6-(3-amino-4-ethylaminophenyl)-4,5-dihydropyridazin-3-one, there are obtained the corresponding 5-methyl-6-(1-ethyl-2-$R^1$-5-benzimidazolyl)-4,5-dihydropyridazin-3-ones, e.g. those with

| | |
|---|---|
| $R^1 =$ | styryl |
| | 2-thienyl, m.p. 199–200° |
| | 2-pyridyl, m.p. 233–234° |
| | 3-pyridyl, m.p. 204–206° |
| | 4-pyridyl, m.p. 229–230°. |

EXAMPLE 3

A mixture of 10.7 g of pyridine-4-aldehyde, 21.8 g of IIa, 19 g of sodium disulfite (Na$_2$S$_2$O$_5$) and 250 ml of ethanol is boiled for 6 hours. It is evaporated, the usual working up is carried out, and "M", dihydrate, m.p. 195°–198° (decomposition), is obtained.

5-Ethyl-6-[2-(4-pyridyl)-5-benzimidazolyl]-4,5-dihydropyridazin-3-one (dihydrochloride-dihydrate, m.p. 299°–302°) an the following 5-ethyl-6-(2-$R^1$-5-benzimidazolyl)-4,5-dihydropyridazin-3-ones are obtained analogously with 5-ethyl-6-(3,4-diaminophenyl)-4,5-dihydropyridazin-3-one:

| | |
|---|---|
| $R^1 =$ | styryl |
| | p-methylstyryl |
| | p-methoxystyryl |
| | 3,4-dimethoxystyryl |
| | p-fluorostyryl |
| | p-chlorostyryl |
| | p-dimethylaminostyryl |
| | 2-pyrryl |
| | 1-methyl-2-pyrryl |
| | 2-furyl |
| | 5-methyl-2-furyl |
| | 3-furyl |
| | 2-thienyl |
| | 3-thienyl |
| | 2-pyridyl |
| | 6-methyl-2-pyridyl |
| | 3-pyridyl |
| | 4-chloro-3-pyridyl |
| | 2,6-dichloro-4-pyridyl |
| | 4-thiazolyl |
| | 4-methyl-2-thiazolyl |

-continued

> 2,4-dimethyl-5-thiazolyl
> 3-pyrazolyl
> 5-methyl-3-pyrazolyl
> 2-imidazolyl
> 4(5)-imidazolyl
> 2-methyl-4(5)-imidazolyl
> 1,2,4-triazol-5-yl
> 4-quinolyl.

6-[2-(4-Pyridyl)-5-benzimidazolyl]-4,5-dihydropyridazin-3-one (hydrochloride, m.p. >320°) and the following 6-(2-R$^1$-5-benzimidazolyl-4,5-dihydropyridazin-3-ones are obtained analgously with 6-(3,4-diaminophenyl)-4,5-dihydropyridazin-3-one:

| R$^1$ = | styryl |
| | p-methylstyryl |
| | p-methoxystyryl |
| R$^1$ = | 3,4-dimethoxystyryl |
| | p-fluorostyryl |
| | p-chlorostyryl |
| | p-dimethylaminostyryl |
| | 2-pyrryl |
| | 1-methyl-2-pyrryl |
| | 2-furyl |
| | 5-methyl-2-furyl |
| | 3-furyl |
| | 2-thienyl |
| | 3-thienyl |
| | 2-pyridyl |
| | 6-methyl-2-pyridyl |
| | 3-pyridyl |
| | 4-chloro-3-pyridyl |
| | 2,6-dichloro-4-pyridyl |
| | 4-thiazolyl |
| | 4-methyl-2-thiazolyl |
| | 2,4-dimethyl-5-thiazolyl |
| | 3-pyrazolyl |
| | 5-methyl-3-pyrazolyl |
| | 2-imidazolyl |
| | 4(5)-imidazolyl |
| | 2-methyl-4(5)-imidazolyl |
| | 1,2,4-triazol-5-yl |
| | 4-quinolyl. |

EXAMPLE 4

A solution of 1 g of 5-methyl-6-(3-amino-4-isonicotinamidophenyl)-4,5-dihydropyridazin-3-one [obtained by reaction of methyl 3-(3-nitro-4-aminobenzoyl)butyrate with isonicotinoyl chloride to give methyl 3-(3-nitro-4-isonicotinamidobenzoyl)butyrate, reaction with hydrazine hydrate to give 5-methyl-6-(3-nitro-4-isonicotinamidophenyl)-4,5-dihydropyridazin-3-one and hydrogenation on Pd-C] in 10 ml of acetic acid is boiled for 1.5 hours, evaporated and the usual working up is carried out. "M", dihydrate, m.p. 195°-198° (decomposition), is obtained.

The other compounds mentioned in Examples 1-3 can be obtained analogously.

EXAMPLE 5

HCl gas is passed for 2 hours into a boiling suspension of 1 g of 5-methyl-6-(3-amino-4-nicotinamidophenyl)-4,5-dihydropyridazin-3-one in 50 ml of isopropanol. After evaporation and the usual working up, 5-methyl-6-[2-(3-pyridyl)-5-benzimidazolyl]-4,5-dihydropyridazin-3-one, dihydrate, decomposition above 173°, is obtained.

4-Methyl-6-[2-(4-pyridyl)-5-benzimidazolyl]-4,5-dihydropyridazin-3-one is obtained analogously from 4-methyl-6-(3-amino-4-isonicotinamidophenyl)-4,5-dihydropyridazin-3- one.

EXAMPLE 6

A mixture of 3.1 g of 3-methyl-4-oxo-4-[2-(4-pyridyl)-5-benzimidazolyl]butyric acid [obtainable from 2-(4-pyridyl)benzimidazol and methylsuccinic anhydride/AlCl$_3$] and 2 g of hydrazine hydrate in 70 ml of acetic acid is stirred at 100° for 2 hours, the usual working up is carried out, and "M", dihydrate, m.p. 195°-198° (decomposition), is obtained.

The following are obtained analogously with the appropriate alkyl hydrazines:

1,5-dimethyl-6-[2-(4-pyridyl)-5-benzimidazolyl]-4,5-dihydropyridazin-3-one, dihydrochloride dihydrate, m.p. 228°-235°.

1-ethyl-5-methyl-6-[2-(4-pyridyl)-5-benzimidazolyl]-4,5-dihydropyridazin-3-one, dimethanesulphonate, m.p. 232°-233°

1-propyl-5-methyl-6-[2-(4-pyridyl)-5-benzimidazolyl]-4,5-dihydropyridazin-3-one 1-isobutyl-5-methyl-6-[2-(4-pyridyl)-5-benzimidazolyl]-4,5-dihydropyridazin-3-one and 1,5-diethyl-6-[2-(4-pyridyl)-5-benzimidazolyl]-4,5-dihydropyridazin-3-one.

EXAMPLE 7

A solution of 1.2 ml of bromine in 12 ml of acetic acid is added dropwise to a solution of 3.42 g of "M" hydrochloride in 100 ml of acetic acid at 70°, with stirring. The temperature is maintained at 70° for 1 hour, and the mixture is evaporated, the usual working up is carried out, and 5-methyl-6-[2-(4-pyridyl)-5-benzimidazolyl]-pyridazin-3-one is obtained. No m.p. up to 330°.

The following 5-methyl-6-(2-R$^1$-5-benzimidazolyl)-pyridazin-3-ones are obtained analogously from the appropriate 4,5-dihydropyridazin-3-ones:

| R$^1$ = | styryl |
| | p-methylstyryl |
| | p-methoxystyryl |
| | 3,4-dimethoxystyryl |
| | p-fluorostyryl |
| | p-chlorostyryl |
| | p-dimethylaminostyryl |
| | 2-pyrryl |
| | 1-methyl-2-pyrryl |
| | 2-furyl |
| | 5-methyl-2-furyl |
| | 3-furyl |
| | 2-thienyl |
| | 3-thienyl |
| | 2-pyridyl |
| R$^1$ = | 3-pyridyl |
| | 4-chloro-3-pyridyl |
| | 2,6-dichloro-4-pyridyl |
| | 4-thiazolyl |
| | 4-methyl-2-thiazolyl |
| | 2,4-dimethyl-5-thiazolyl |
| | 3-pyrazolyl |
| | 5-methyl-3-pyrazolyl |
| | 2-imidazolyl |
| | 4(5)-imidazolyl |
| | 2-methyl-4(5)-imidazolyl |
| | 1,2,4-triazol-5-yl |
| | 4-quinolyl, | and the corresponding 6-(2-R$^1$-5-benzimidazolyl)-pyridazinones, their 5-ethyl derivatives and the corresponding 5-methyl-6-(1-methyl-2-R$^1$-5-benzimidazolyl)-pyridazinones, as well as:

4-methyl-6-[2-(4-pyridyl)-5-benzimidazolyl]-pyridazin-3-one
1,5-dimethyl-6-[2-(4-pyridyl)-5-benzimidazolyl]-pyridazin-3-one and
1,5-diethyl-6-[2-(4-pyridyl)-5-benzimidazolyl]-pyridazin-3-one.

EXAMPLE 8

A mixture of 3.05 g of "M", 2.5 g of 2,3-dichloro-5,6-dicyano-1,4-benzoquinone (DDQ) and 25 ml of dioxane is boiled under $N_2$ for 10 hours. The mixture is evaporated, the usual working up is carried out, and 5-methyl-6-[2-(4-pyridyl)-5-benzimidazolyl]pyridazin-3-one is obtained.

EXAMPLE 9

A solution of 1 g of 5-methyl-6-[2-(5-nitro-2-furyl)-5-benzimidazolyl]-4,5-dihydropyridazin-3-one in 30 ml of methanol is hydrogenated to completion on 0.2 g of 5% Pd-C at 20° and under 1 bar. The mixture is filtered, the filtrate is evaporated, and 5-methyl-6-[2-(5-amino-2-furyl)-5-benzimidazolyl]-4,5-dihydropyridazin-3-one is obtained.

EXAMPLE 10

0.3 ml of acetyl chloride in 3 ml of chloroform is added to a solution of 309 mg of 5-methyl-6-[2-(5-amino-2-furyl)-5-benzimidazolyl]-4,5-dihydropyridazin-3-one and 0.2 ml of triethylamine in 10 ml of chloroform, and the mixture is boiled for 3 hours. The usual working up is carried out, and 5-methyl-6-[2-(5-acetamido-2-furyl)-5-benzimidazolyl]-4,5-dihydropyridazin-3-one is obtained.

EXAMPLE 11

A mixture of 1 g of 5-methyl-6-(2-p-methoxycarbonylstyryl-5-benzimidazolyl)-4,5-dihydropyridazin-3-one and 60 ml of 10% sodium hydroxide solution is stirred at 20° for 12 hours. After acidification with HCl and carrying out the usual working up, 5-methyl-6-(2-p-carboxystyryl-5-benzimidazolyl)-4,5-dihydropyridazin-3-one hydrochloride is obtained.

EXAMPLE 12

A mixture of 10.7 g of pyridine-4-carboxaldehyde, 21.8 g of IIa, 15.4 g of benzylidene-malodinitrile and 500 ml of ethanol is boiled for 3 hours. After the usual working up, "M" is obtained, dihydrate, m.p. 195°-198° (decomposition).

Analogously there is obtained:
With (+)-IIa [obtainable by reaction of (−)-3-(4-chloro-3-nitrobenzoyl)-butyric acid with hydrazine to (+)-5-methyl-6-(4-chloro-3-nitrophenyl)-4,5-dihydropyridazin-3-one, conversion to (+)-5-methyl-6-(4-benzylamino-3-nitrophenyl)-4,5-dihydropyridazin-3-one with benzylamine and hydrogenation in methanolic hydrogen chloride solution]: (+)-"M", m.p. 216°-220°. Methanesulphonate, m.p. 280°-285°; $[\alpha]_D^{20} +238,0°$ (in water).

With (−)-IIa: (−)-"M", m.p. 219°-223°. Methanesulphonate, m.p. 280°-285°; $[\alpha]_D^{20} -237,9°$ (in water).

The examples which follow relate to pharmaceutical formulations which contain compounds of the formula I or their acid addition salts:

Example A: tablets

A mixture of 1 kg of "M", 4 kg of lactose, 1.2 kg of potato starch, 0.2 kg of talc and 0.1 kg of magnesium stearate is compressed in the usual manner to form tablets, in such a way that each tablet contains 10 mg of active compound.

Example B: coated tablets

Tablets are compressed in analogy to Example A, and are then coated in the usual manner with a coating of sucrose, potato starch, talc, tragacanth and colorant.

Example C: capsules 1 kg of 5-methyl-6-[2-(3-thienyl)-5-benzimidazolyl]-4,5-dihydropyridazin-3-one hydrochloride is dispensed in a usual manner into hard gelatin capsules, so that each capsule contains 5 mg of active compound.

Example D: ampoules

A solution of 1 kg of 5-methyl-6-[2-(2-pyridyl)-5-benzimidazolyl]-4,5-dihydropyridazin-3-one hydrochloride monohydrate in 100 ml of double-distilled water is sterilized by filtration, dispensed into ampoules, freeze-dried under sterile conditions, and sterile closure is carried out. Each ampoule contains 2 mg of active compound.

It is possible to obtain tablets, coated tablets, capsules and ampoules which contain one or more of the other active compounds of the formula I and/or their physiologically acceptable acid addition salts analogously.

During the investigation of the positive inotropic activity on the isolated papillary muscle of the guinea pig (methods in analogy to those described in Arzneimittelforschung, l.c.), the following compounds of formula I were found to be particularly active:

5-methyl-6-[2-(4-pyridyl)-5-benzimidazolyl]-4,5-dihydropyridazin-3-one, dihydrate 5-methyl-6-(2-p-methoxystyryl-5-benzimidazolyl)-4,5-dihydropyridazin-3-one, hydrochloride, monohydrate 5-methyl-6-[2-(3-pyrazolyl)-5-benzimidazolyl]-4,5-dihydropyridazin-3-one, hydrochloride, hemihydrate 5-methyl-6-(2-p-dimethylaminostyryl-5-benzimidazolyl)-4,5-dihydropyridazin-3-one, hemihydrate 5-methyl-6-(2-styryl-5-benzimidazolyl)-4,5-dihydropyridazin-3-one, hydrochloride.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A benzimidazolylpyridazinone of the formula

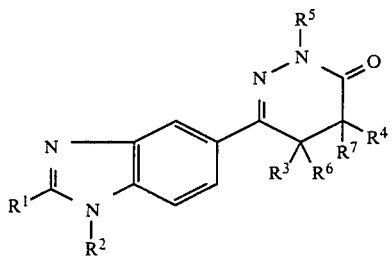

wherein
R[1] is styryl, a mononuclear or binuclear heteroaryl group which contains 1–4 heterotoms, or styryl or one of said heteroaryl groups each of which is single or multiply substituted by alkyl, alkoxy, alkylthio, halogen, OH, SH, amino, alkylamino, dialkylamino, acylamino of 1–8 carbon atoms, nitro, COOH, COOalkyl or CN, each of R[2], R[3], R[4] and R[5] independently is H or alkyl, and R[6] and R[7] are each H, or together are a C—C bond, and in which each alkyl and alkoxy group is of 1–4 C atoms and acyl is alkanoyl, benzoyl, picolinoyl, nicotinoyl, isonicotinoyl, or benzoyl, picolinoyl, nicotinoyl or isonicotinoyl each substituted by the substituents listed for styryl except acylamino, or a pharmacologically acceptable salt thereof.

2. A compound of claim 1 wherein R[1] is 2-, 3- or 4-pyridyl, 2- or 3-thienyl, 2- or 3-furyl, 1-methyl-2-pyrryl, styryl, p-dimethylaminostyryl or 3,4-dimethoxystyryl.

3. A compound of claim 1 wherein R[2], R[4] and R[5] each independently is H or CH₃.

4. A compound of claim 1 wherein R[2], R[4] and R[5] each is H.

5. A compound of claim wherein R[3] is H, CH₃ or C₂H₅.

6. A compound of claim 1 wherein R[6] and R[7] is H.

7. A compound of claim 1 wherein R[1] is 2-, 3- or 4-pyridyl, 2- or 3-thienyl, 2- or 3-furyl, 1-methyl-2-pyrryl, styryl, p-dimethylaminostyryl or 3,4-dimethoxystyryl, R[2], R[4] and R[5] are each H or CH₃, and R[3] is H, CH₃ or C₂H₅.

8. A compound of claim 1 wherein R[1] is 2-, 3-, or 4-pyridyl or 2-or 3-thienyl, R[4], R[4] and R[5] are each H or CH₃, and R[3] is H, CH₃ or C₂H₅.

9. A compound of claim 1 wherein R[1] is 2-, 3- or 4-pyridyl or 2-or 3-thienyl, R[2], R[4] and R[5] are each H or CH₃, R[3] is H, CH₃ or C₂H₅, and R[6] and R[7] are each H.

10. A compound of claim 1 wherein R[1] is 2-, 3- or 4-pyridyl or 2- or 3-thienyl, R[2], R[4] and R[5] are each H or CH₃, and R[3] is H, CH₃ or C₂H₅, and R[6] and R[7] together are a C—C bond.

11. A compound of claim 1 wherein R[1] is 2-, 3- or 4-pyridyl, 2- or 3-thienyl, 2- or 3-furyl, 1-methyl-2-pyrryl, styryl, p-dimethylaminostyryl or 3,4-dimethoxystyryl, R[2] is H or CH₃, R[3] is CH₃ or C₂H₅, and R[4], R[5], R[6] and R[7] are each H.

12. A compound of claim 1 wherein R[1] is 2-, 3- or 4-pyryidyl or 2- or 3-thienyl, R[2] is H or CH₃, R[3] is CH₃ or C₂H₅, and R[4], R[5], R[6] and R[7] are each H.

13. (a) 5-Methyl-6-[2-(4-pyridyl)-5-benzimidazolyl]-4,5-dihydro-pyridazin-3-one; (b) 5-Methyl-6-[2-(3-pyridyl)-5-benzimidazolyl-4,5-dihydro-pyridazin-3-one; (c) 5-Methyl-6-[2-(2-pyridyl)-5-benzimidazolyl]-4,5-dihydro-pyridazin-3-one; (d) 5-Methyl-6-[2-(3-thienyl)-5-benzimidazolyl]-4,5-dihydro-pyridazin-3-one; (e) 5Methyl-6-[1-methyl-2-(4-pyridyl)-5-benzimidazolyl]-4,5-dihydro-pyridazin-3-one, each a compound of claim 1.

14. A pharmaceutical composition comprising a compound of claim 1 and a pharmaceutically acceptable carrier.

15. A composition of claim 14 wherein the amount of said compound is 1–100 mg.

16. A method of treating cardiac insufficiency comprising administering a compound of claim 1.

17. A method of achieving a positive inotropic effect comprising administering a compound of claim 1.

18. A method of achieving an antithrombotic effect comprising administering a compound of claim 1.

19. A compound of claim 1 wherein the total number of ring atoms in said heteroaryl group is 3–14, each ring contains 3–8 ring atoms and said heteroatoms are O, N or S.

20. A benzimidazolylpyridazinone of the formula:

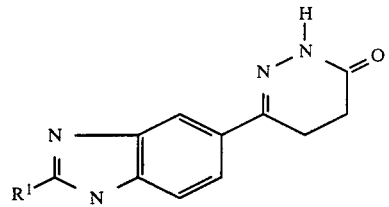

wherein R[1] is a mononuclear or binuclear heteroaryl group having 1–4 heteroatoms bonded via a carbon atom, each heteroaryl is substituted by alkyl, amino or alkanoylamino.

* * * * *